United States Patent
Wang et al.

(10) Patent No.: US 10,995,103 B2
(45) Date of Patent: May 4, 2021

(54) SUBSTITUTED BORIC ACID COMPOUND, PHARMACEUTICAL COMPOSITION COMPRISING SAME, AND APPLICATION THEREOF

(71) Applicant: Shenzhen TargetRx, Inc., Guangdong (CN)

(72) Inventors: Yihan Wang, Shenzhen (CN); Jiuyang Zhao, Shenzhen (CN)

(73) Assignee: Shenzhen TargetRx, Inc., Guangdong (CN)

( * ) Notice: Subject to any disclaimer, the term of this patent is extended or adjusted under 35 U.S.C. 154(b) by 0 days.

(21) Appl. No.: 16/320,436

(22) PCT Filed: Jul. 24, 2017

(86) PCT No.: PCT/CN2017/094044
§ 371 (c)(1),
(2) Date: Jan. 24, 2019

(87) PCT Pub. No.: WO2018/019196
PCT Pub. Date: Feb. 1, 2018

(65) Prior Publication Data
US 2019/0263835 A1      Aug. 29, 2019

(30) Foreign Application Priority Data

Jul. 25, 2016   (CN) .......................... 201610592116.8

(51) Int. Cl.

| | |
|---|---|
| *A61K 31/69* | (2006.01) |
| *A61K 9/00* | (2006.01) |
| *C07B 59/00* | (2006.01) |
| *C07F 5/02* | (2006.01) |
| *A61P 13/12* | (2006.01) |
| *A61P 29/00* | (2006.01) |
| *A61P 35/00* | (2006.01) |
| *A61P 35/02* | (2006.01) |
| *A61P 37/00* | (2006.01) |
| *A61P 9/00* | (2006.01) |
| *C07K 5/06* | (2006.01) |
| *C07H 23/00* | (2006.01) |

(52) U.S. Cl.
CPC ............. *C07F 5/02* (2013.01); *A61K 31/69* (2013.01); *A61P 9/00* (2018.01); *A61P 13/12* (2018.01); *A61P 29/00* (2018.01); *A61P 35/00* (2018.01); *A61P 35/02* (2018.01); *A61P 37/00* (2018.01); *C07B 59/004* (2013.01); *C07H 23/00* (2013.01); *C07K 5/06* (2013.01); *A61K 9/0019* (2013.01); *A61K 9/0053* (2013.01); *C07B 2200/05* (2013.01)

(58) Field of Classification Search
CPC ........ C07F 5/02; C07H 23/00; C07B 2200/05
See application file for complete search history.

(56) References Cited

U.S. PATENT DOCUMENTS

| | | | |
|---|---|---|---|
| 7,442,830 B1 * | 10/2008 | Olhava | .................. C07F 5/025 562/450 |
| 2009/0076031 A1 | 3/2009 | Czarnik | |
| 2009/0325903 A1 | 12/2009 | Elliott et al. | |
| 2011/0301124 A1 | 12/2011 | Olhava et al. | |

FOREIGN PATENT DOCUMENTS

| | | |
|---|---|---|
| CA | 2695082 A1 | 2/2009 |
| CN | 101772507 A | 7/2010 |
| CN | 102066386 A | 5/2011 |
| CN | 106916177 A * | 7/2017 |
| EP | 3210987 A1 | 8/2017 |
| JP | 2010-535759 A | 11/2010 |
| JP | 2014-097964 A | 5/2014 |
| JP | 2015-117185 A | 6/2015 |
| WO | WO-2009020448 A1 * | 2/2009 .............. C07F 5/025 |

(Continued)

OTHER PUBLICATIONS

Zhu et al. CN106916177A English machine translation obtained online Mar. 16, 2020 from dialog.com. (Year: 2020).*
International Search Report and Written Opinion dated Oct. 23, 2017 for Application No. PCT/CN2017/094044.
International Preliminary Report on Patentability dated Feb. 7, 2019 for Application No. PCT/CN2017/094044.
Extended European Search Report for Application No. 17833499.1, dated May 21, 2019.
Foster, Deuterium isotope effects in the metabolism of drugs and xenobiotics: implications for drug design. Adv Drug Res. 1985;14. 40 pages.
Gant, Using deuterium in drug discovery: leaving the label in the drug. J Med Chem. May 8, 2014;57(9):3595-611. doi: 10.1021/jm4007998. Epub Dec. 2, 2013.

(Continued)

*Primary Examiner* — Amanda L. Aguirre
(74) *Attorney, Agent, or Firm* — Wolf, Greenfield & Sacks, P.C.

(57) ABSTRACT

A substituted boric acid compound, a pharmaceutical composition including the same, and an application thereof. The substituted boric acid compound is a compound represented by formula (I), or a crystal form, a pharmaceutically acceptable salt, a prodrug, a stereoisomer, a hydrate, or a solvent compound thereof. The boric acid compound has proteasome inhibitory activity, good pharmacodynamic/pharmacokinetic performance, good applicability, and high safety, and can be used for preparing drugs for treating diseases related to proteasomes.

(1)

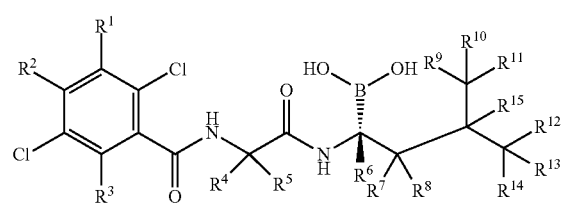

16 Claims, No Drawings

(56) References Cited

FOREIGN PATENT DOCUMENTS

WO          2013/180149  A1    12/2013
WO    WO 2014/011971  A2     1/2014

OTHER PUBLICATIONS

Harbeson et al., Deuterium Medicinal Chemistry: A New Approach to Drug Discovery and Development. Medchem News. May 2014;24(2):8-22. Doi: 10.14894/medchem.24.2_8.
Li et al., Synthesis of four isotopically labeled forms of a proteasome inhibitor, bortezomib. J Label Compd Radiopharm. Apr.-May 2007;50(5-6):402-6. Epub Jul. 30, 2007.
Liu, Deuterated Drug Progress. Medicine and Chemical Industry. Apr. 30, 2016;42(4):199, 238.
Declaration of Vinita Uttamsingh. Feb. 1, 2012. 5 pages.
Harbeson et al., Deuterium in Drug Discovery and Development. Annual Reports in Medicinal Chemistry. 2011;46:403-417. 10.1016/B978-0-12-386009-5.00003-5.
Shao et al., Derivatives of tramadol for increased duration of effect. Bioorg Med Chem Lett. 2006;16(3):691-694. doi:10.1016/j.bmcl.2005.10.024.
Japanese Office Action for Application No. 2019-503546, dated Jul. 14, 2020.
Li et al., Boronic Acid-Containing Proteasome Inhibitors: Alert to Potential Pharmaceutical Bioactivation. Chem Res Toxicol. Apr. 15, 2013;26(4):608-15. doi: 10.1021/tx400032n. Epub Apr. 2, 2013.
JP2019-503546, Jul. 14, 2020, Japanese Office Action and English translation thereof.

\* cited by examiner

SUBSTITUTED BORIC ACID COMPOUND, PHARMACEUTICAL COMPOSITION COMPRISING SAME, AND APPLICATION THEREOF

CROSS REFERENCE TO RELATED APPLICATIONS

The present application is a national application of PCT/CN2017/094044 filed on Jul. 24, 2017, which claims the priority of the Chinese Patent Application No. 201610592116.8 filed on Jul. 25, 2016.

FIELD OF THE INVENTION

The present disclosure belongs to the pharmaceutical field. In particular, disclosed herein are a substituted boronic acid compound and a pharmaceutical composition comprising the same, which can be used in the manufacture of a medicament for treating a proteasome-mediated disease.

BACKGROUND OF THE INVENTION

Proteasome is a large multivalent complex enzyme, which is involved in many important physiological and biochemical processes in the cell, such as DNA repairing, cell cycle running, signal transduction, antigen presentation, protein transmembrane localization, and the like, and plays a major role in balancing important intracellular enzymes. The function of the proteasome is achieved by the ubiquitin-proteasome pathway (UPP). UPP not only catalyzes the degradation of abnormal proteins, but also participates in many regulation and regeneration and processing of proteins. The catalytic process of these proteins involves an important biochemical mechanism for the pathogenesis of human disease.

Proteasome inhibitors affect the expression of cell growth-related proteins, cytokines and signaling molecules by inhibiting the activity of proteasomes, thereby interfering with the original proliferation, differentiation and apoptosis of cells, and inhibiting the growth of tumor cells more significantly.

Proteasome inhibitors mainly include peptide aldehydes, peptide boronic acids, peptide epoxy ketones, peptide vinyl sulfones, beta lactones and other kind of compounds. The peptide boronic acid proteasome inhibitor Bortezomib (trade name VELCADE) is the first proteasome inhibitor for clinical use and was approved by the US Food and Drug Administration (FDA) for the treatment of multiple myeloma (MM) and mantle cell lymphoma (MCL) in 2003 and 2006, respectively. The peptide epoxy ketone proteasome inhibitor Carfilzomib (trade name Kyprolis) was approved by the FDA in 2012 for the treatment of multiple myeloma and became the second marketed proteasome type antitumor drug. The peptide boronic acid proteasome inhibitor Ixazomib citrate (trade name Ninlaro) was approved by the FDA in 2015 for the treatment of multiple myeloma and became the second marketed peptide boronic acid proteasome inhibitor. The marketed and reported boronic acid proteasome inhibitors, such as those in WO2005/021558, WO2005/016859, WO2006/086600, WO2009/02044, WO2010/012222, WO2011/109355, WO2011/026349, WO2011/087822, WO2013/092979, and the like, are proteasome inhibitors have a peptide skeleton, which have low stability in vivo, short half-life in plasma, and rapid clearance (Miller et al. J Med Chem, 2015, 58: 2036-41).

Therefore, there is still a need in the art to develop proteasome inhibitors that have inhibitory activity against the proteasome or better pharmacodynamic properties.

SUMMARY OF THE INVENTION

Regarding the above technical problems, disclosed herein are a proteasome inhibitor, a pharmaceutical composition and the use thereof, which have better proteasome inhibitory activity and/or have better pharmacodynamic/pharmacokinetic properties.

In this regard, the technical solution adopted herein is:

a proteasome inhibitor, which is a substituted boronic acid compound represented by Formula (I), or a crystalline form, a pharmaceutically acceptable salt, a hydrate or a solvate thereof,

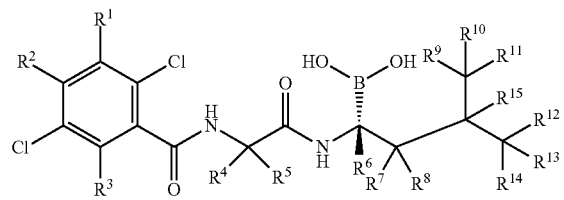

Formula (I)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are each independently hydrogen, deuterium, or halogen;

provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterated or deuterium.

As a further embodiment disclosed herein, $R^1$, $R^2$ and $R^3$ are each independently deuterium or hydrogen.

As a further embodiment disclosed herein, $R^4$ and $R^5$ are each independently deuterium or hydrogen.

As a further embodiment disclosed herein, $R^6$ is deuterium.

As a further embodiment disclosed herein, $R^7$ and $R^8$ are each independently deuterium or hydrogen.

As a further embodiment disclosed herein, $R^9$, $R^{10}$, $R^{11}$, $R^{12}$, $R^{13}$, $R^{14}$, and $R^{15}$ are each independently deuterium or hydrogen.

As a further embodiment disclosed herein, the compound can be selected from, but is not limited to, the group consisting of the following compounds or a pharmaceutically acceptable salt thereof:

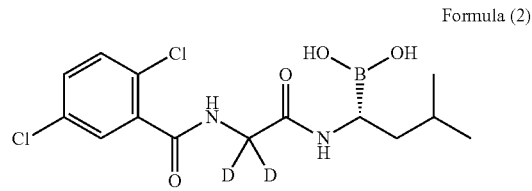

Formula (2)

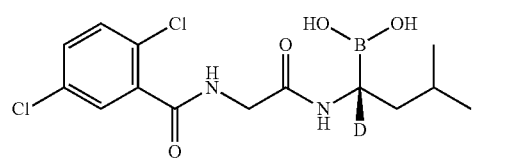

Formula (3)

Formula (4)
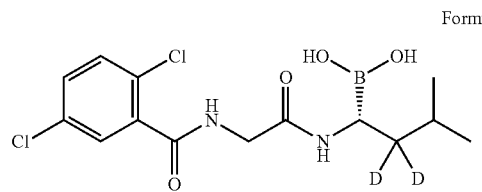
Formula (5)
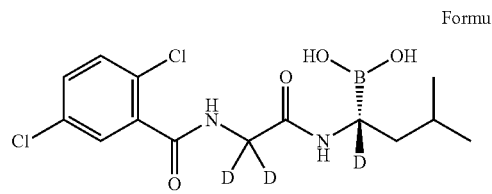
Formula (6)
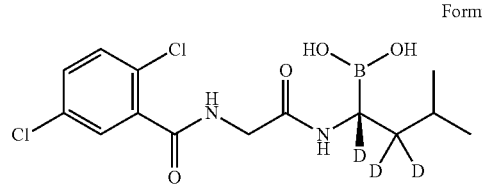
Formula (7)
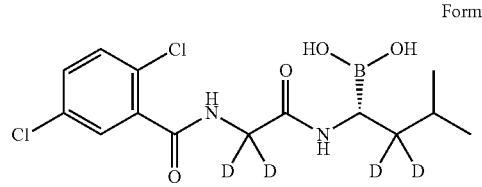
Formula (8)
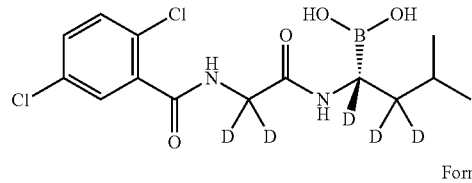
Formula (9)
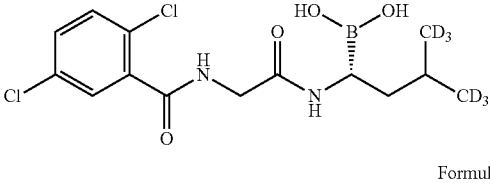
Formula (10)
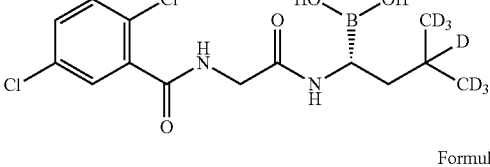
Formula (11)
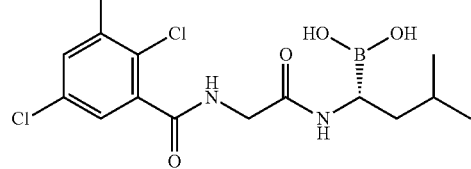
Formula (12)
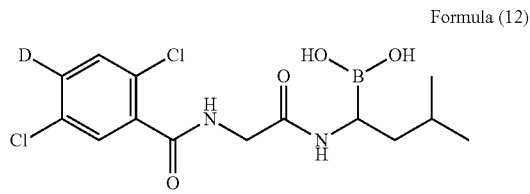
Formula (13)
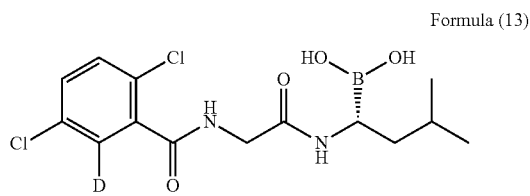
Formula (14)
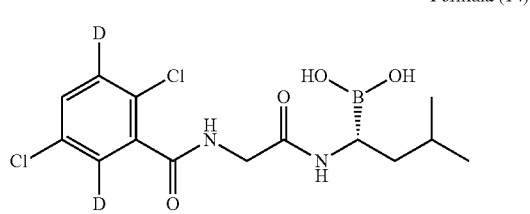
Formula (15)
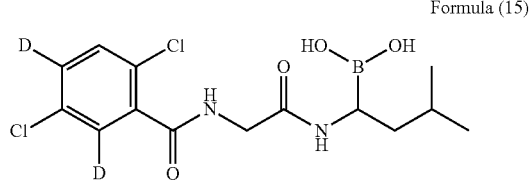
Formula (16)
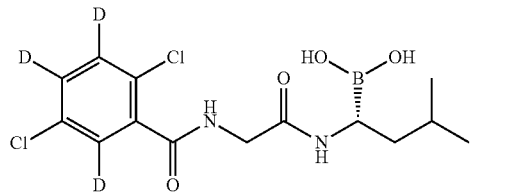
Formula (17)
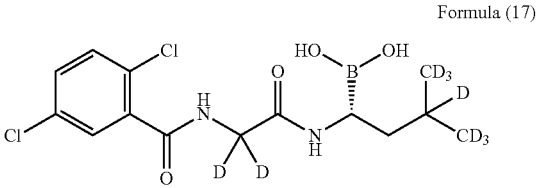
Formula (18)
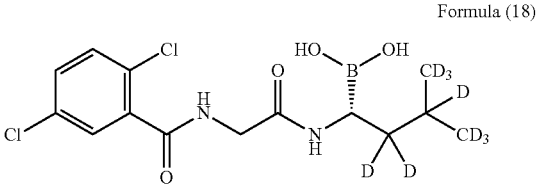
Formula (19)
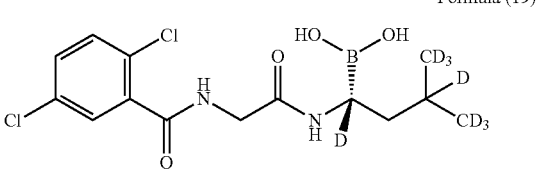

-continued

Formula (20)
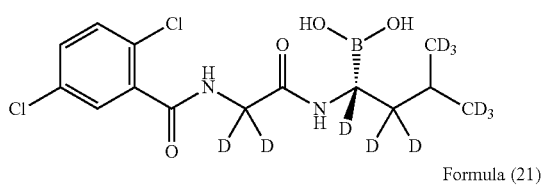

Formula (21)
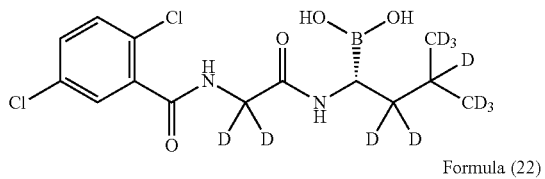

Formula (22)
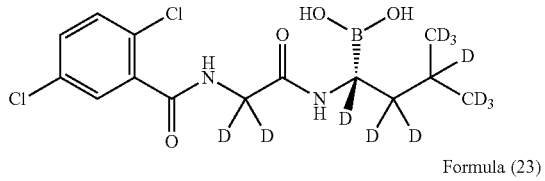

Formula (23)
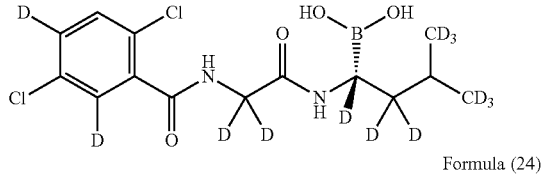

Formula (24)
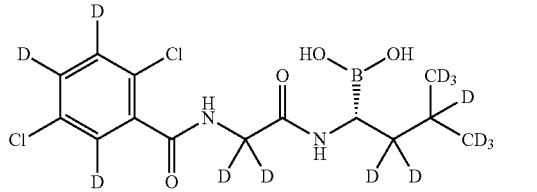

Formula (25)
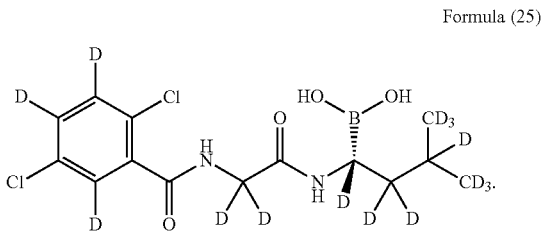 [SMILES: [2H]c1c([2H])c(Cl)c(C(=O)NC([2H])([2H])C(=O)N[C@@]([2H])(B(O)O)C([2H])([2H])C([2H])(C([2H])([2H])[2H])C([2H])([2H])[2H])c([2H])c1Cl]

With this technical solution, the shape and volume of the deuterium in the drug molecule are substantially the same as those of the hydrogen. If the hydrogen in the drug molecule is selectively replaced with deuterium, the deuterated drug generally retains the original biological activity and selectivity. At the same time, the inventors have confirmed through experiments that the binding of carbon-deuterium bonds is more stable than the binding of carbon-hydrogen bonds, which can directly affect the absorption, distribution, metabolism and excretion of some drugs, thereby improving the efficacy, safety and tolerability of the drugs.

Preferably, the content of deuterium isotope in the deuterated position is at least greater than the natural content of deuterium isotope (0.015%), preferably greater than 30%, more preferably greater than 50%, more preferably greater than 75%, more preferably greater than 95%, and more preferably greater than 99%.

Specifically, in the present disclosure, the content of the deuterium isotope in each deuterated position of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is at least 5%, preferably greater than 10%, more preferably greater than 15%, more preferably greater than 20%, more preferably greater than 25%, more preferably greater than 30%, more preferably greater than 35%, more preferably greater than 40%, more preferably greater than 45%, more preferably greater than 50%, more preferably greater than 55%, more preferably greater than 60%, more preferably greater than 65%, more preferably greater than 70%, more preferably greater than 75%, more preferably greater than 80%, more preferably greater than 85%, more preferably greater than 90%, more preferably greater than 95%, and more preferably greater than 99%.

In another embodiment, in $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ of the compound of Formula (I), at least one R contains deuterium, more preferably two Rs contain deuterium, more preferably three Rs contain deuterium, more preferably four Rs contain deuterium, more preferably five Rs contain deuterium, more preferably six Rs contain deuterium, more preferably seven Rs contain deuterium, more preferably eight Rs contain deuterium, more preferably nine Rs contain deuterium, more preferably ten Rs contain deuterium, more preferably eleven Rs contain deuterium, more preferably twelve Rs contain deuterium, more preferably thirteen Rs contain deuterium, more preferably fourteen Rs contain deuterium, and more preferably fifteen Rs contain deuterium.

In another preferred embodiment, the compound does not include a non-deuterated compound.

Disclosed herein is also a pharmaceutical composition comprising a pharmaceutically acceptable carrier and the proteasome inhibitor as described above, or a crystalline form, a pharmaceutically acceptable salt, a hydrate or a solvate, a stereoisomer, a prodrug or an isotopic variation thereof.

As a further embodiment disclosed herein, the pharmaceutically acceptable carrier comprises at least one of glidant, sweetener, diluent, preservative, dye/colorant, flavor enhancer, surfactant, wetting agent, dispersant, disintegrant, suspending agent, stabilizer, isotonic agent, solvent and emulsifier.

As a further embodiment disclosed herein, the pharmaceutical composition is a tablet, a pill, a capsule, a powder, a granule, a cream, an emulsion, a suspension, a solution, a suppository, an injection, an inhalant, a gel, a microsphere or an aerosol.

Typical routes of administration of the pharmaceutical compositions disclosed herein include, but are not limited to, oral, rectal, transmucosal, enteral, topical, transdermal, inhalation, parenteral, sublingual, intravaginal, intranasal, intraocular, intraperitoneal, intramuscular, subcutaneous, or intravenous administration. Oral administration or injection administration is preferred.

The pharmaceutical composition disclosed herein can be produced by a method known in the art, such as a conventional mixing method, a dissolution method, a granulation method, a sugar-coating method, a pulverization method, an emulsification method, a freeze-drying method, and the like.

Disclosed herein is also a process for the preparation of a pharmaceutical composition comprising the step of: mixing a pharmaceutically acceptable carrier with a proteasome inhibitor as described above, or a crystalline form, a pharmaceutically acceptable salt, a hydrate or a solvate thereof to form a pharmaceutical composition.

The compound disclosed herein has enzyme inhibitory activity against proteasome and is therefore expected to be useful as a therapeutic agent for treating a patient suffering from a disease or condition which is treated by inhibiting the proteasome or by increasing its peptide substrate content. Accordingly, one aspect disclosed herein relates to a method of treating a patient suffering from a disease or condition which is treated by inhibiting the proteasome, comprising administering to the patient a therapeutically effective amount of a compound disclosed herein. Another aspect disclosed herein relates to a method of treating a cardiovascular disease, comprising administering to the patient a therapeutically effective amount of a compound disclosed herein. Another aspect disclosed herein relates to a method of treating hypertension or inhibiting the proteasome in a mammal, comprising administering to the mammal a proteasome inhibitory amount of a compound disclosed herein.

Disclosed herein is also the use of the substituted boronic acid compound as described above as a proteasome inhibitor, that is, the compound disclosed herein can be used in the manufacture of a medicament for a proteasome-mediated disease.

The proteasome-mediated diseases disclosed herein include inflammatory conditions (for example, rheumatoid arthritis, inflammatory bowel disease, asthma, chronic obstructive pulmonary disease (COPD), osteoarthritis, skin diseases (for example, atopic dermatitis, psoriasis)), vascular proliferative disorders (for example, atherosclerosis, restenosis), ocular proliferative disorders (for example, diabetic retinopathy), benign proliferative lesions (for example, vascular cancer), autoimmune diseases (for example, multiple sclerosis, tissue and organ rejection), and inflammation associated with infection (for example, immune response), neurodegenerative disorders (for example, Alzheimer's disease, Parkinson's disease, motor neuron disease, neuropathic pain, triplet repeat disorder, astrocytoma and neurodegeneration caused by alcoholic liver disease), ischemic injury (for example, stroke) and cachexia (for example, accelerated muscle protein degradation with various physiological and pathological conditions (for example, nerve damage, hunger strike, fever, acidosis, HIV infection, cancer, and certain endocrine disease)).

The compounds disclosed herein are particularly useful for the treatment of cancer. The term "cancer" as used herein refers to a cellular disorder characterized by uncontrolled or dysregulated cell proliferation, decreased cell differentiation, the ability to inappropriately invade surrounding tissues, or the ability to form new growth at ectopic sites. The term "cancer" includes, but is not limited to, solid tumors or hematological tumors. The term "cancer" encompasses diseases of the skin, tissues, organs, bones, cartilage, blood and blood vessels. The term "cancer" also includes primary and metastatic cancers. The tumor cells of the cancer are preferably one or more of leukemia cell myeloma cells, non-small cell lung cancer cells, breast cancer cells, and ovarian cancer cells.

It is to be understood that within the scope disclosed herein, the various technical features disclosed hereinbefore and the technical features specifically described hereinafter (as in examples) may be combined with each other to constitute a new or preferred technical solution. Due to space limitations, we will not repeat them here.

As used herein, unless otherwise specified, "halogen" means F, Cl, Br, and I. More preferably, a halogen atom is selected from the group consisting of F, Cl and Br.

As used herein, unless otherwise specified, "deuterated" means that one or more hydrogens in the compound or group are replaced by deuterium; "deuterated" may be monosubstituted, disubstituted, polysubstituted or fully substituted with deuteriums. The terms "one or more deuterated" are used interchangeably with "deuterated one or more times".

As used herein, unless otherwise specified, "non-deuterated compound" means a compound containing a deuterium atom with a ratio not higher than the natural content of deuterium isotope (0.015%).

The pharmaceutically acceptable salts include inorganic and organic salts. A preferred class of salts are the salts of the compounds disclosed herein with acids. Suitable acids for forming salts include, but are not limited to, mineral acids such as hydrochloric acid, hydrobromic acid, hydrofluoric acid, sulfuric acid, nitric acid, phosphoric acid and the like; organic acids such as formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, p-toluenesulfonic acid, benzenesulfonic acid, naphthalenesulfonic acid and the like; amino acids such as proline, phenylalanine, aspartic acid, glutamic acid and the like. Another preferred class of salts are the salts of the compounds disclosed herein with bases, such as alkali metal salts (for example, sodium or potassium salts), alkaline earth metal salts (for example, magnesium or calcium salts), ammonium salts (for example, lower alkanolammonium salts and other pharmaceutically acceptable amine salts), such as methylamine salts, ethylamine salts, propylamine salts, dimethylamine salts, trimethylamine salts, diethylamine salts, triethylamine salts, tert-butylamine salts, ethylenediamine salts, hydroxyethylamine salts, dihydroxyethylamine salts, trihydroxyethylamine salts, and amine salts formed with morpholine, piperazine, and lysine, respectively.

The term "solvate" refers to a complex formed by the coordination of a compound disclosed herein with a solvent molecule in a particular ratio. "Hydrate" means a complex formed by the coordination of a compound disclosed herein with water.

Compared with the prior art, the beneficial effects of the compound disclosed herein are: the compound disclosed herein has excellent inhibition to the proteasome; the technique of deuteration changes the metabolism of the compound in the organism, rendering the compound with better pharmacokinetic parameter characteristics. In this case, the dosage can be changed and a long-acting preparation can be formed to improve the applicability; by replacing the hydrogen atom in the compound with deuterium, the drug concentration of the compound in the animal body can be increased due to the deuterium isotope effect, and thus the therapeutic effect of the drug can be improved; by replacing the hydrogen atom in the compound with deuterium, certain metabolites can be suppressed and the safety of the compound can be increased.

DETAILED DESCRIPTION OF THE EMBODIMENTS

The methods of preparing the compound of Formula (I) disclosed herein are more specifically described below, but these specific methods do not constitute any limitation to the present invention. The compounds disclosed herein may also be conveniently prepared by combining various synthetic methods described in the specification or known in the art, and such combinations can be readily made by those skilled in the art to which the present invention pertains.

Example 1 Preparation of (R)-(1-(2-(2,5-dichlorobenzamido)-2,2-d2-acetamido)-3-methylbutyl) boronic acid (Compound I-1)

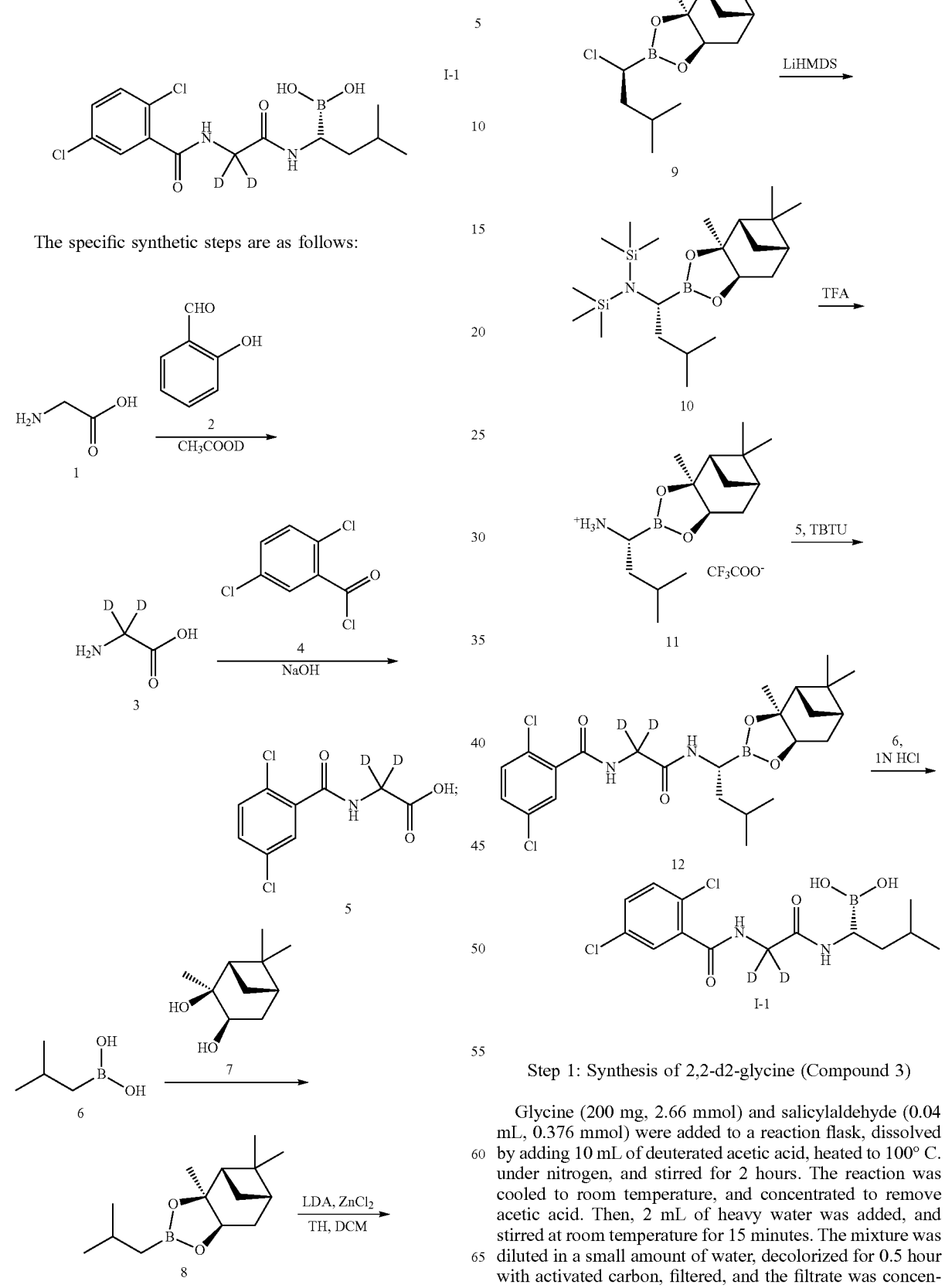

The specific synthetic steps are as follows:

Step 1: Synthesis of 2,2-d2-glycine (Compound 3)

Glycine (200 mg, 2.66 mmol) and salicylaldehyde (0.04 mL, 0.376 mmol) were added to a reaction flask, dissolved by adding 10 mL of deuterated acetic acid, heated to 100° C. under nitrogen, and stirred for 2 hours. The reaction was cooled to room temperature, and concentrated to remove acetic acid. Then, 2 mL of heavy water was added, and stirred at room temperature for 15 minutes. The mixture was diluted in a small amount of water, decolorized for 0.5 hour with activated carbon, filtered, and the filtrate was concentrated to dryness. A small amount of methanol was added, and a white solid was precipitated under stirring, which was filtered, and dried in vacuo to give a product (176.7 mg, yield: 88%). LC-MS (APCI): m/z=78.1 (M+1)+.

Step 2: Synthesis of 2,5-[(dichlorobenzoyl)amino]-d2-acetic Acid (Compound 5)

The compound 3 (131 mg, 1.7 mmol) and sodium hydroxide (212.5 mg, 5.31 mmol) were added to a reaction flask, and dissolved by adding 2 mL of water. A solution of 2,5-dichlorobenzoyl chloride (176.7 mg, 0.85 mmol) in 1 mL tetrahydrofuran was added dropwise in an ice bath, and the reaction was stirred for 1 hour after the addition. After TLC detected the reaction was completed, the pH of the reaction was adjusted to acidic with a dilute hydrochloric acid, and a white solid was precipitated, which was filtered, washed with ice water, and dried in vacuo to give a product (200 mg, yield: 94.5%). LC-MS (APCI): m/z=250.3 (M+1)+.

Step 3: Synthesis of 2-methylpropylboronic acid-(+)-pinanediol Ester (Compound 8)

Isobutylboronic acid (510.5 mg, 5 mmol) and (1S,2S,3R,5S)-(+)-2,3-pinanediol (850.65 mg, 5 mmol) were added to a reaction flask, and dissolved by adding 5 mL of n-heptane. The reaction was stirred at room temperature for 2 hours. After TLC detected the reaction was completed, the mixture was washed with brine, dried over anhydrous sodium sulfate, filtered, concentrated, and dried in vacuo to give a product (1.1 g, yield: 93.14%).

Step 4: Synthesis of (S)-1-chloro-3-methylbutylboronic acid-(+)-pinanediol Ester (Compound 9)

The compound 8 (1.1 g, 4.66 mmol) was added to a reaction flask, and dissolved by adding 6.5 mL of anhydrous tetrahydrofuran and 1.54 mL of anhydrous dichloromethane. The temperature was lowered to −78° C. under nitrogen, and a 2 M solution of lithium diisopropylamide (LDA, 4.66 mL, 9.32 mmol) was slowly added dropwise. After the addition, the reaction was stirred for 2 hours. A 1 M solution of zinc chloride in tetrahydrofuran (8.16 mL, 8.16 mmol) was slowly added dropwise. After the addition, the reaction was reacted at the low temperature for 2 hours. After TLC detected the reaction was completed, a small amount of 10% dilute sulfuric acid was added to quench the reaction, and the organic phase was separated. The aqueous phase was extracted with n-hexane, and the organic phases were combined, washed with brine, and concentrated. The residue was purified by silica gel column chromatography and dried in vacuo to give a product (1.31 g, yield: 98.9%). LC-MS (APCI): m/z=285.5 (M+1)+.

Step 5: Synthesis of (R)-1-(hexamethyldisilanyl) amino-3-methylbutylboronic Acid Pinanediol Ester (Compound 10)

The compound 9 (1.35 g, 4.75 mmol) was added to a reaction flask, dissolved by adding 10 mL of anhydrous tetrahydrofuran, and the temperature was lowered to −40° C. under nitrogen. Lithium bis(trimethylsilyl)amide (LiHMDS, 5.7 mL, 5.7 mmol) was slowly added dropwise. After the addition, the reaction was stirred for 1 hour, and then the reaction was warmed to room temperature and reacted for 1 hour. After TLC detected the reaction was completed, the mixture was filtered through a plug of silica gel, and the filtrate was evaporated to dryness to give a product (1.9 g, yield: 97.7%), which was used directly in the next step.

Step 6: Synthesis of L-leucine Boronic Acid-(+)-pinanediol Ester Trifluoroacetate Salt (Compound 11)

The compound 10 (1.7 g, 4.15 mmol) was added to a dry reaction flask, dissolved by adding 6 mL of diisopropyl ether, and the temperature was lowered to −15° C. under nitrogen.

Trifluoroacetic acid (TFA, 1.89 g, 16.6 mmol) was slowly added dropwise. After the addition, the reaction was kept at this temperature and reacted for 2 hours, and then allowed to warm to room temperature and reacted overnight. The mixture was filtered, and the filter cake was washed with diisopropyl ether and dried in vacuo to give a white solid (620 mg, yield: 39.5%). LC-MS (APCI): m/z=266.2 (M+1)+.

Step 7: Synthesis of 2,5-dichloro-N-[2-({(1R)-3-methyl-1-[(3aS,4S,6S,7aR)-3a,5,5-trimethylhexahydro-4,6-methylene-1,3,2-benzodioxaborolan-2-yl] butyl}amino)-2-oxa-1,1-d2-ethyl]benzamide (Compound 12)

The compound 5 (100 mg, 0.402 mmol) and the compound 11 (152.3 mg, 0.402 mmol) were added to a reaction flask, O-benzotriazol-N,N,N',N'-tetramethyluronium tetrafluoroborate (TBTU, 142 mg, 0.44 mmol) was added under nitrogen, and the substances were dissolved by adding 2 ml of anhydrous N,N-dimethylformamide (DMF), and N,N-diisopropylethylamine (DIPEA, 156 mg, 1.21 mmol) was added under ice bath. After the addition, the reaction was warmed to room temperature and stirred for 1 hour. After TLC detected the reaction was completed, the mixture was diluted with a small amount of water and extracted 3-4 times with EtOAc. The organic phases were combined, washed with brine, concentrated and then purified by silica gel column chromatography to give a product (196 mg, yield: 98.2%). LC-MS (APCI): m/z=497.5 (M+1)+.

Step 8: Synthesis of (R)-(1-(2-(2,5-dichlorobenzamido)-2,2-d2-acetamido)-3-methylbutyl)boronic Acid (Compound I-1)

The compound 12 (196 mg, 0.395 mmol) and isobutylboronic acid (104.8 mg, 1.03 mmol) were added to a reaction flask, and dissolved by adding 2 mL of methanol and 2 mL of n-hexane, 1N hydrochloric acid (0.5 mL, 0.5 mmol) was then added, and the reaction was stirred at room temperature under nitrogen protection overnight. After TLC detected the reaction was completed, the methanol layer was separated, washed three times with n-heptane, concentrated to dryness under reduced pressure, dissolved by adding 2N sodium hydroxide and washed three times with dichloromethane. The aqueous phase was adjusted to pH 2-3 with concentrated hydrochloric acid and extracted with dichloromethane for 3-4 times. The organic phases were combined, washed with brine, concentrated, and purified by silica gel column chromatography. The product was dried and weighed 85 mg (yield: 59.4%). LC-MS (APCI): m/z=345.2 (M+1-$H_2O$). $^1$H NMR (400 MHz, DMSO) δ 8.93 (s, 1H), 8.71 (d, J=7.8 Hz, 1H), 7.65 (s, 1H), 7.55 (d, J=1.3

Hz, 2H), 2.64 (s, 1H), 1.61 (dd, J=13.3, 6.5 Hz, 1H), 1.40-1.32 (m, 1H), 1.26 (s, 1H), 0.85-0.80 (m, 6H).

Example 2 Preparation of (R)-(1-(2-(2,5-dichlorobenzamido)acetamido)-1-d-3-methylbutyl)boronic Acid (Compound I-2)

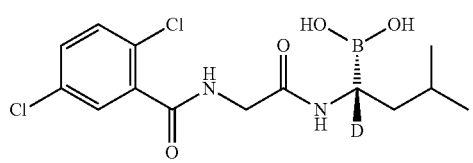

The specific synthetic steps are as follows:

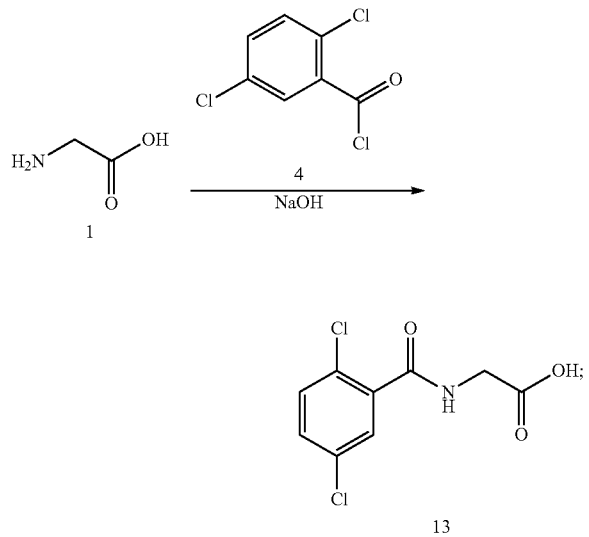

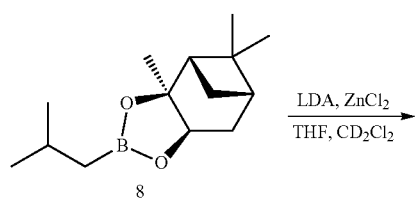

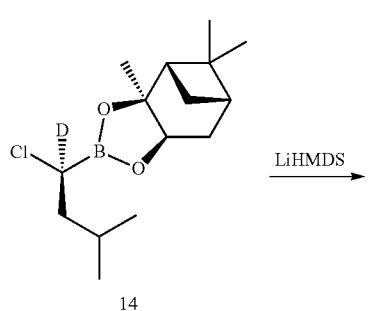

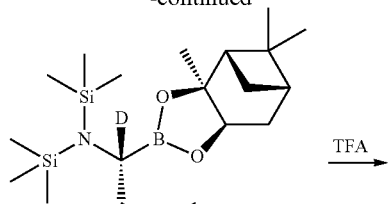

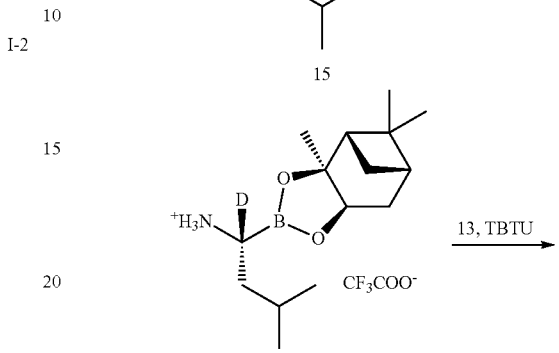

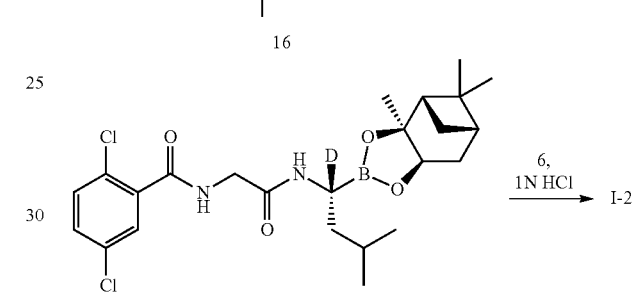

Step 1: Synthesis of 2,5-[(dichlorobenzoyl)amino]acetic Acid (Compound 13)

Glycine (1.125 g, 15 mmol) and sodium hydroxide (750 mg, 18.75 mmol) were added to a reaction flask, and dissolved by adding 7.5 mL of water. A solution of 2,5-dichlorobenzoyl chloride (623.7 mg, 3.0 mmol) in 1 mL of tetrahydrofuran was added dropwise in an ice bath. After the addition, the reaction was stirred for 1 hour. After TLC detected the reaction was completed, the pH was adjusted to acidic with dilute hydrochloric acid, and a white solid was precipitated, which was filtered, washed with ice water and dried in vacuo to give a product (675 mg, yield: 91.1%). LC-MS (APCI): m/z=248.3 (M+1)$^+$.

Step 2: Synthesis of (S)-1-chloro-1-d-3-methylbutylboronic acid-(+)-pinanediol Ester (Compound 14)

The compound 8 (1.1 g, 4.66 mmol) was added to a reaction flask, and dissolved by adding 6.5 mL of anhydrous tetrahydrofuran (THF) and 1.54 mL of deuterated dichloromethane. The temperature was lowered to −78° C. under nitrogen protection, and a 2 M solution of LDA (4.66 mL, 9.32 mmol) was slowly added dropwise. After the addition, the reaction was stirred for 2 h. A 1 M solution of zinc chloride in tetrahydrofuran (8.16 mL, 8.16 mmol) was slowly added dropwise. After the addition, the reaction was continued for 2 hours at the low temperature. After TLC detected the reaction was completed, a small amount of 10% dilute sulfuric acid was added to quench the reaction, and the organic phase was separated. The aqueous phase was extracted with n-hexane, and the organic phases were combined, washed with brine, and concentrated. The residue was purified by silica gel column chromatography and dried in vacuo to give a product (1.29 g, yield: 97.0%). LC-MS (APCI): m/z=286.2 (M+1)+.

Step 3: Synthesis of (R)-1-(hexamethyldisilanyl) amino-1-d-3-methylbutylboronic Acid Pinanediol Ester (Compound 15)

The compound 14 (1.29 g, 4.52 mmol) was added to a reaction flask, dissolved by adding 9 mL of anhydrous tetrahydrofuran, and the temperature was lowered to −40° C. under nitrogen protection. Lithium bis(trimethylsilyl)amide (5.4 mL, 5.4 mmol) was slowly added dropwise. After the addition, the reaction was stirred for 1 hour, and then warmed to room temperature and reacted for 1 hour. After TLC detected the reaction was completed, the mixture was filtered through a plug of silica gel, and the filtrate was evaporated to dryness to give a product (1.6 g, yield: 86.3%), which was directly used in the next step.

Step 4: Synthesis of 1-d-L-leucine boronic acid-(+)-pinanediol Ester Trifluoroacetate Salt (Compound 16)

The compound 15 (1.6 g, 3.8 mmol) was added to a dry reaction flask, dissolved by adding 6 mL of diisopropyl ether, and the temperature was lowered to −15° C. under nitrogen protection. Trifluoroacetic acid (1.75 g, 15.4 mmol) was slowly added dropwise. After the addition, the reaction was reacted at this temperature for 2 hours and then allowed to warm to room temperature and reacted overnight. After filtration, the filter cake was washed with diisopropyl ether and dried in vacuo to give a white solid (561 mg, yield: 38.9%). LC-MS (APCI): m/z=267.7 (M+1)+.

Step 5: Synthesis of 2,5-dichloro-N-[2-({(1R)-3-methyl-1-[(3aS,4S,6S,7aR)-3a,5,5-trimethylhexahydro-4,6-methylene-1,3,2-benzodioxaborolan-2-yl]-1-d-butyl}amino)-2-oxaethyl]benzamide (Compound) 17)

The compound 16 (100 mg, 0.405 mmol) and the compound 13 (154 mg, 0.405 mmol) were added to a reaction flask, TBTU (143 mg, 0.46 mmol) was added under nitrogen protection, and dissolved by adding 2 mL of anhydrous DMF. DIPEA (157 mg, 1.21 mmol) was added dropwise in an ice bath. After the addition, the reaction was warmed to room temperature and stirred for 1 hour. After TLC detected the reaction was completed, the mixture was diluted with a small amount of water and extracted 3-4 times with EtOAc. The organic phases were combined, washed with brine, concentrated, and then purified by silica gel column chromatography to give a product (148 mg, yield: 73.8%). LC-MS (APCI): m/z=496.5 (M+1)+.

Step 6: Synthesis of (R)-(1-(2-(2,5-dichlorobenzamido)acetamido)-1-d-3-methylbutyl)boronic Acid (Compound I-2)

The compound 17 (148 mg, 0.3 mmol) and isobutylboronic acid (79.63 mg, 0.78 mmol) were added to a reaction flask, and dissolved by adding 2 mL of methanol and 2 mL of n-hexane. 1N hydrochloric acid (0.4 mL, 0.4 mmol) was added, and the reaction was stirred at room temperature under nitrogen protection overnight. After TLC detected the reaction was completed, the methanol layer was separated, washed three times with n-heptane, concentrated to dryness under reduced pressure, which was dissolved by adding a small amount of 2N sodium hydroxide and washed three times with dichloromethane. The aqueous phase was adjusted to pH 2-3 with concentrated hydrochloric acid and extracted with dichloromethane for 3-4 times. The organic phases were combined, washed with brine, concentrated and then purified by silica gel column chromatography. The product was dried and weighed 61 mg (yield: 56.3%). LC-MS (APCI): m/z=344.3 (M+1-H$_2$O). $^1$H NMR (400 MHz, DMSO) δ 8.94 (t, J=5.9 Hz, 1H), 8.69 (s, 1H), 7.65 (s, 1H), 7.55 (d, J=1.4 Hz, 2H), 4.02 (d, J=5.8 Hz, 2H), 1.62 (dt, J=13.3, 6.7 Hz, 1H), 1.35 (dd, J=13.0, 6.7 Hz, 1H), 1.25 (d, J=7.2 Hz, 1H), 0.86-0.79 (m, 6H).

Example 3 Preparation of (R)-(1-(2-(2,5-dichlorobenzamido)acetamido)-2,2-d2-3-methylbutyl)boronic Acid (Compound I-3)

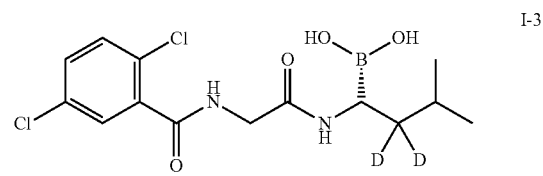

The specific synthetic steps are as follows:

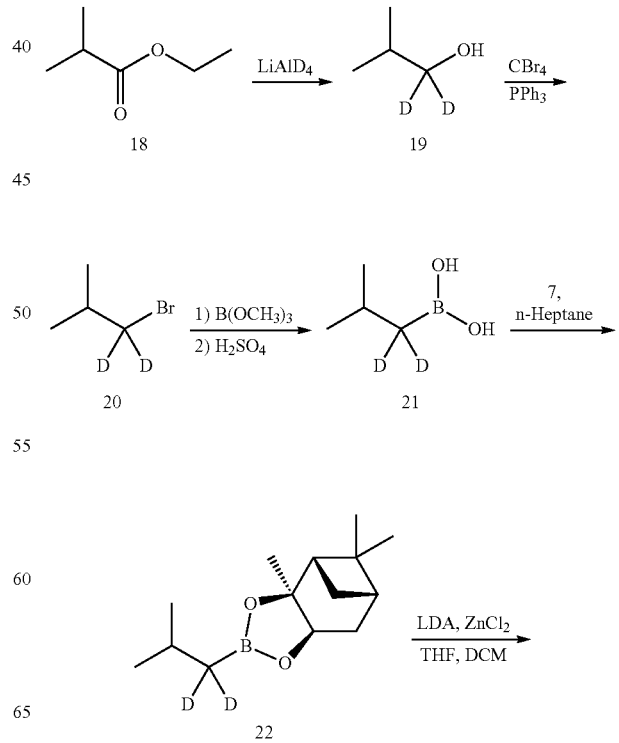

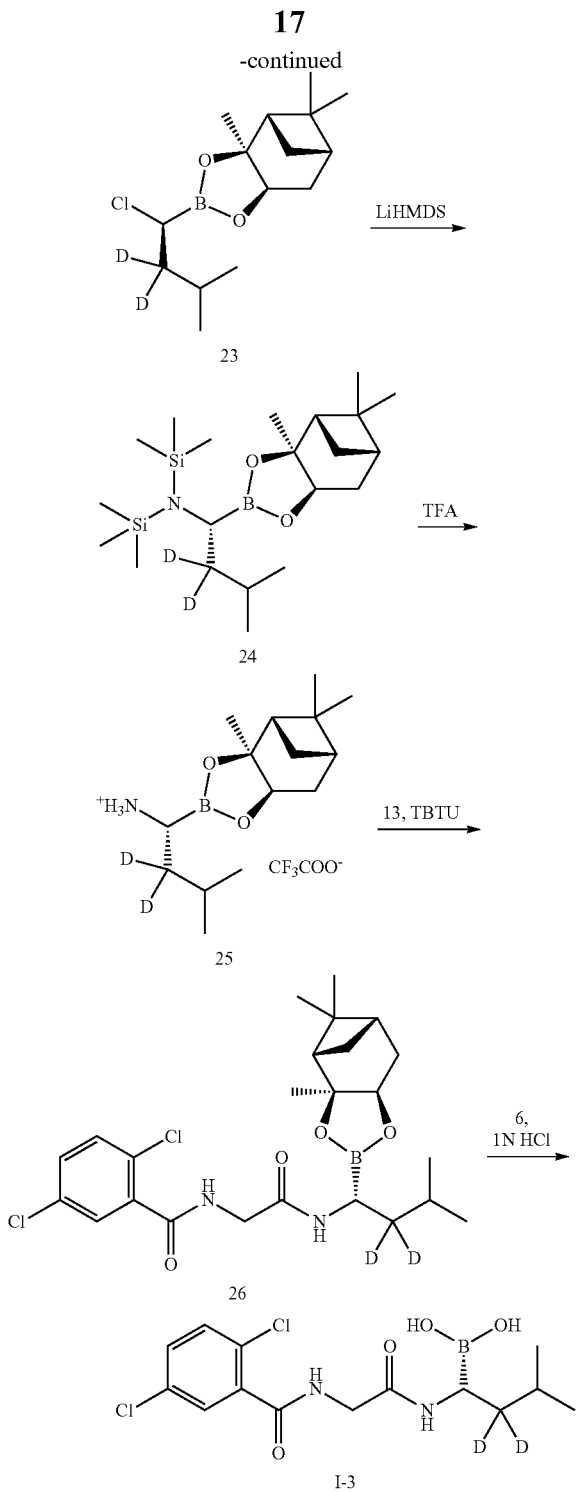

removed by filtration, and the filtrate was concentrated to give a product (246 mg, yield: 64.73%), which was directly used in the next step.

Step 2: Synthesis of 1,1-d2-bromoisobutane (Compound 20)

The compound 19 (850 mg, 11.17 mmol) and carbon tetrabromide (3.7 g, 11.17 mmol) were dissolved in dichloromethane (15 mL), and Triphenylphosphine ($PPh_3$, 2.93 g, 11.17 mmol) was added portionwise in an ice bath. The reaction was stirred at low temperature for 1 hour under nitrogen protection, and then warmed to room temperature and reacted for 1 hour. After TLC detected the reaction was completed, a small amount of water was added to quench the reaction, and the aqueous phase was extracted three times with dichloromethane. The organic phases were combined, washed with brine, concentrated, and then purified by column chromatography to give a product (865 mg, yield: 56.2%).

Step 3: Synthesis of 1,1-d2-isobutylboronic Acid (Compound 21)

The compound 20 (120 mg, 0.87 mmol) was dissolved in 5 mL of anhydrous THF, and magnesium turning (104.3 mg, 4.35 mmol) and a catalytic amount of iodine (1 granule) were added under nitrogen protection. The mixture was heated to 50° C. and stirred for 3 hours. After cooling to room temperature, the Grignard reagent was taken out with a syringe, and slowly added dropwise to trimethyl borate (180.8 mg, 1.74 mmol) in 5 mL of anhydrous THF at −15° C., and the reaction was stirred for 1 hour under nitrogen protection. After TLC detected the reaction was completed, the reaction was warmed to room temperature, and the pH was adjusted to 2-3 with dilute hydrochloric acid. The mixture was stirred for 15 minutes, and the organic phase was separated. The aqueous phase was extracted three times with ethyl acetate. The organic phases were combined, washed with brine and concentrated. The residue was purified by column chromatography to give a product (64 mg, yield: 70.7%).

Step 4: Synthesis of 1,1-d2-2-methylpropylboronic acid-(+)-pinanediol Ester (Compound 22)

The compound 21 (110 mg, 1.06 mmol) and (1S, 2S, 3R, 5S)-(+)-2,3-pinanediol (179.8 mg, 1.06 mmol) were added to a reaction flask, and dissolved by adding 3 mL of n-heptane. The reaction was stirred at room temperature for 2 hours. After TLC detected the reaction was completed, the mixture was washed with brine, dried over anhydrous sodium sulfate, filtered, concentrated, and dried in vacuo to give a product (238 mg, yield: 94.2%).

Step 5: Synthesis of (S)-1-chloro-2,2-d2-3-methylbutylboronic Acid-(+)-pinanediol Ester (Compound 23)

The compound 22 (238 mg, 1.0 mmol) was added to a reaction flask, and dissolved by adding 2 mL of anhydrous tetrahydrofuran and 0.5 mL of anhydrous dichloromethane. The temperature was lowered to −78° C. under nitrogen protection. A 2 M LDA solution (1.0 mL, 2.0 mmol) was slowly added dropwise. After the addition, the reaction was stirred for 2 hours. A 1 M solution of zinc chloride in tetrahydrofuran (1.75 mL, 1.75 mmol) was slowly added Step 1: Synthesis of 1,1-d2-2-methylpropanol (Compound 19)

Ethyl isobutyrate (580.8 mg, 5 mmol) was dissolved in anhydrous THF (20 mL), and $LiAlD_4$ (230.9 mg, 5.5 mmol) was added portionwise in an ice bath. After the addition, the mixture was warmed to room temperature and reacted overnight. After TLC detected the reaction was completed, the reaction was quenched by adding sodium sulfate decahydrate under the ice bath. The insoluble material was dropwise. After the addition, the reaction was reacted for 2 hours at the low temperature. After TLC detected the reaction was completed, a small amount of 10% dilute sulfuric acid was added to quench the reaction, and the organic phase was separated. The aqueous phase was extracted with n-hexane. The organic phases were combined, washed with brine, concentrated, purified by silica gel column chromatography and dried in vacuo to give a product (265 mg, yield: 92.6%). LC-MS (APCI): m/z=287.7 (M+1)$^+$.

Step 6: Synthesis of (R)-1-(hexamethyldisilanyl) amino-2,2-d2-3-methylbutylboronic Acid Pinanediol Ester (Compound 24)

The compound 23 (265 mg, 0.93 mmol) was added to a reaction flask, dissolved by adding 3 mL of anhydrous tetrahydrofuran, and lowered to −40° C. under nitrogen protection. Lithium bis(trimethylsilyl)amide (1.11 mL, 1.11 mmol) was slowly added dropwise. After the addition, the reaction was stirred for 1 hour, and then warmed to room temperature and reacted for 1 hour. After TLC detected the reaction was completed, the mixture was filtered through a plug of silica gel, and the filtrate was evaporated to dryness to give a product (382.5 mg, yield: 100%), which was directly used in the next step.

Step 7: Synthesis of L-d2-leucine Boronic Acid-(+)-pinanediol Ester Trifluoroacetate Salt (Compound 25)

The compound 24 (382.5 mg, 0.93 mmol) was added to a dry reaction flask, dissolved by adding 3 mL of diisopropyl ether, and lowered to −15° C. under nitrogen protection. Trifluoroacetic acid (424.1 mg, 3.72 mmol) was slowly added dropwise. After the addition, the reaction was reacted at this temperature for 2 hours and then warmed to room temperature and reacted overnight. After the filtration, the cake was washed with diisopropyl ether and dried in vacuo to give a white solid (202 mg, yield: 57.1%). LC-MS (APCI): m/z=268.2 (M+1)$^+$.

Step 8: Synthesis of 2,5-dichloro-N-[2-({(1R)-2,2-d2-3-methyl-1-[(3aS,4S,6S,7aR)-3a,5,5-trimethyl-hexahydro-4,6-methylene-1,3,2-benzodioxaborolan-2-yl]butyl}amino)-2-oxaethyl]benzamide (Compound 26)

The compound 13 (100 mg, 0.402 mmol) and the compound 25 (152.4 mg, 0.402 mmol) were added to a reaction flask, TBTU (142 mg, 0.44 mmol) was added under nitrogen protection, and dissolved by adding 2 mL of anhydrous DMF. DIPEA (156 mg, 1.21 mmol) was added dropwise under an ice bath. After the addition, the reaction was warmed to room temperature and stirred for 1 hour. After TLC detected the reaction was completed, the mixture was diluted with a small amount of water and extracted 3-4 times with EtOAc. The organic phases were combined, washed with brine, concentrated and then purified by silica gel column chromatography to give a product (183 mg, yield: 91.9%). LC-MS (APCI): m/z=497.4 (M+1)$^+$.

Step 9: Synthesis of (R)-(1-(2-(2,5-dichlorobenzamido)acetamido)-2,2-d2-3-methylbutyl)boronic Acid (Compound I-3)

The compound 26 (183 mg, 0.369 mmol) and isobutylboronic acid (97.9 mg, 0.96 mmol) were added to a reaction flask, and dissolved by adding 2 mL of methanol and 2 mL of n-hexane. 1N hydrochloric acid (0.5 ml, 0.5 mmol) was added, and the reaction was stirred at room temperature under nitrogen protection overnight. After TLC detected the reaction was completed, the methanol layer was separated, washed three times with n-heptane, concentrated to dryness under reduced pressure, which was dissolved by adding a small amount of 2N sodium hydroxide, and washed three times with dichloromethane. The aqueous phase was adjusted to pH 2-3 with concentrated hydrochloric acid and extracted with dichloromethane for 3-4 times. The organic phases were combined, washed with brine, concentrated and then purified by silica gel column chromatography. The product was dried and weighed 75 mg (yield: 56.4%). LC-MS (APCI): m/z=345.2 (M+1-H$_2$O). $^1$H NMR (400 MHz, DMSO) δ 8.94 (t, J=5.9 Hz, 1H), 8.69 (s, 1H), 7.65 (s, 1H), 7.55 (d, J=1.4 Hz, 2H), 4.02 (d, J=5.8 Hz, 2H), 2.64 (s, 1H), 1.26 (m, 1H), 0.86-0.79 (m, 6H).

Example 4 Preparation of (R)-(1-(2-(2,5-dichlorobenzamido)-2,2-d2-acetamido)-1-d-3-methylbutyl) boronic Acid (Compound I-4)

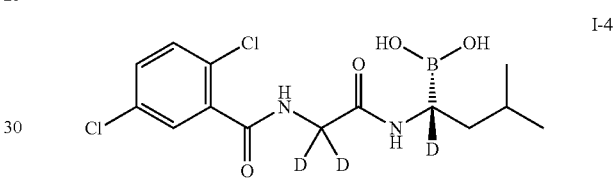

The specific synthetic steps are as follows:

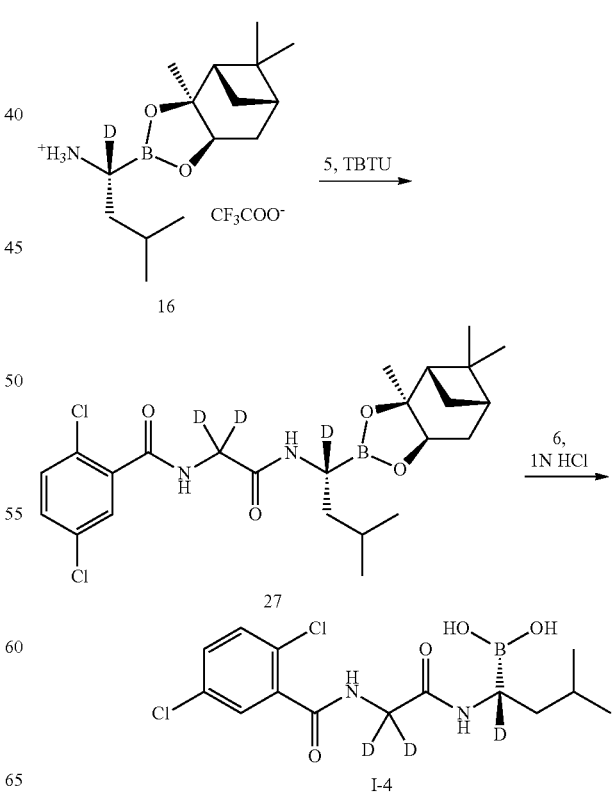

Step 1: Synthesis of 2,5-dichloro-N-[2-({(1(1R)-3-methyl-1-[(3aS,4S,6S,7aR)-3a,5,5-trimethylhexahydro-4,6-methylene-1,3,2-benzodioxaborolan-2-yl]-1-d1-butyl}amino)-2-oxa-1,1-d2-ethyl]benzylamide (Compound 27)

The compound 5 (100 mg, 0.402 mmol) and the compound 16 (154 mg, 0.402 mmol) were added to a reaction flask, TBTU (142 mg, 0.44 mmol) was added under nitrogen protection, and dissolved by adding 2 mL of anhydrous DMF. DIPEA (156 mg, 1.21 mmol) was added dropwise in an ice bath. After the addition, the reaction was warmed to room temperature and stirred for 1 hour. After TLC detected the reaction was completed, the mixture was diluted with a small amount of water and extracted 3-4 times with EtOAc. The organic phases were combined, washed with brine, concentrated and then purified by silica gel column chromatography to give a product (199 mg, yield: 99%). LC-MS (APCI): m/z=498.2 (M+1)$^+$.

Step 2: Synthesis of (R)-(1-(2-(2,5-dichlorobenzamido)-2,2-d2-acetamido)-1-d-3-methylbutyl)boronic Acid (Compound I-4)

The compound 27 (203 mg, 0.408 mmol) and isobutylboronic acid (108.4 mg, 1.06 mmol) were added to a reaction flask, and dissolved by adding 2 mL of methanol and 2 mL of n-hexane. 1N hydrochloric acid (0.5 mL, 0.5 mmol) was added, and the reaction was stirred at room temperature under nitrogen protection overnight. After TLC detected the reaction was completed, the methanol layer was separated, washed three times with n-heptane, concentrated to dryness under reduced pressure, which was dissolved by adding 2N sodium hydroxide, and washed three times with dichloromethane. The aqueous phase was adjusted to pH 2-3 with concentrated hydrochloric acid and extracted 3-4 times with dichloromethane. The organic phases were combined, washed with brine, concentrated, and then purified by silica gel column chromatography. The product was dried and weighed 96 mg (yield: 64.8%). LC-MS (APCI): m/z=346.4 (M+1-H$_2$O). $^1$H NMR (400 MHz, DMSO) δ 8.93 (s, 1H), 8.71 (d, J=11.4 Hz, 1H), 7.65 (s, 1H), 7.55 (d, J=1.3 Hz, 2H), 1.61 (dd, J=13.3, 6.6 Hz, 1H), 1.35 (dd, J=13.0, 7.0 Hz, 1H), 1.25 (d, J=7.1 Hz, 1H), 0.83 (dd, J=6.5, 1.9 Hz, 6H).

Example 5 Preparation of (R)-(1-(2-(2,5-dichlorobenzamido)acetamido)-1-d-2,2-d2-3-methylbutyl)boronic Acid (Compound I-5)

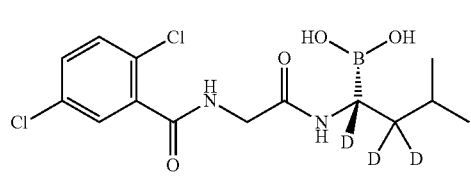

The specific synthetic steps are as follows:

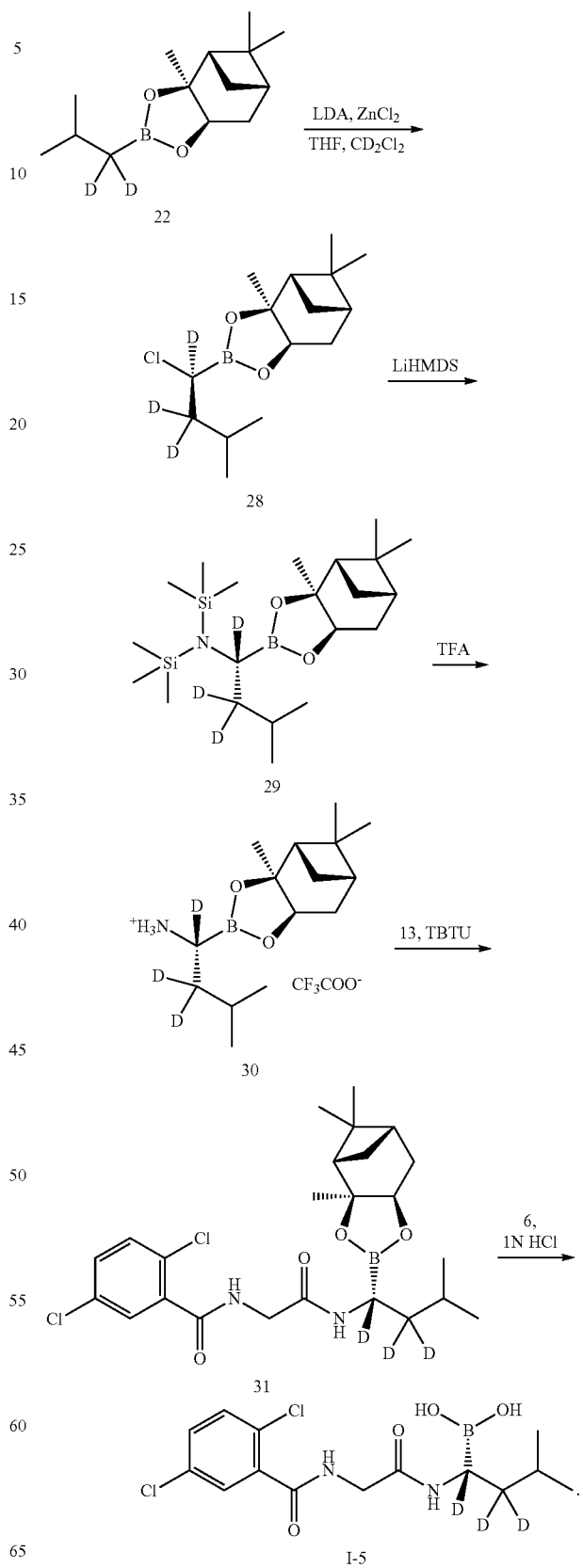

Step 1: Synthesis of (S)-1-chloro-1-d1-2,2-d2-3-methylbutylboronic Acid-(+)-pinanediol Ester (Compound 28)

The compound 22 (238 mg, 1.0 mmol) was added to a reaction flask, and dissolved by adding 2 mL of anhydrous tetrahydrofuran and 0.5 mL of deuterated dichloromethane. The temperature was lowered to −78° C. under nitrogen protection. A 2 M LDA solution (1.0 mL, 2.0 mmol) was slowly added dropwise. After the addition, the reaction was stirred for 2 hours. A 1 M solution of zinc chloride in tetrahydrofuran (1.75 mL, 1.75 mmol) was slowly added dropwise. After the addition, the mixture was reacted at the low temperature for 2 hours. After TLC detected the reaction was completed, a small amount of 10% dilute sulfuric acid was added to quench the reaction, and the organic phase was separated. The aqueous phase was extracted with n-hexane. The organic phases were combined, washed with brine, concentrated, and then purified by silica gel column chromatography, and dried in vacuo to give a product (200 mg, yield: 69.7%). LC-MS (APCI): m/z=288.1 (M+1)$^+$.

Step 2: Synthesis of (R)-1-(hexamethyldisilanyl) amino-1-d1-2,2-d2-3-methylbutylboronic Acid Pinanediol Ester (Compound 29)

The compound 28 (200 mg, 0.70 mmol) was added to a reaction flask, dissolved by adding 3 mL of anhydrous tetrahydrofuran, and lowered to −40° C. under nitrogen protection. Lithium bis(trimethylsilyl)amide (0.84 mL, 0.84 mmol) was slowly added dropwise. After the addition, the reaction was stirred for 1 hour, and then warmed to room temperature and reacted for 1 hour. After TLC detected the reaction was completed, the mixture was filtered through a plug of silica gel, and the filtrate was evaporated to dryness to give a product (288.6 mg, yield: 100%), which was directly used in the next step.

Step 3: Synthesis of L-d3-leucine Boronic Acid-(+)-pinanediol Ester Trifluoroacetate Salt (Compound 30)

The compound 29 (288.6 mg, 0.7 mmol) was added to a dry reaction flask, dissolved by adding 3 mL of diisopropyl ether, and lowered to −15° C. under nitrogen protection. Trifluoroacetic acid (319.2 mg, 2.8 mmol) was slowly added dropwise. After the addition, the mixture was reacted at this temperature for 2 hours, and then warmed to room temperature and reacted overnight. After filtration, the filter cake was washed with diisopropyl ether and dried in vacuo to give a white solid (95 mg, yield: 35.6%). LC-MS (APCI): m/z=269.3 (M+1)$^+$.

Step 4: Synthesis of 2,5-dichloro-N-[2-({(1R)-1-d1-2,2-d2-3-methyl-1-[(3aS,4S,6S,7aR)-3a,5,5-trimethylhexahydro-4,6-methylene-1,3,2-benzodioxaborolan-2-yl]butyl}amino)-2-oxaethyl]benzamide (Compound 31)

The compound 13 (56 mg, 0.226 mmol) and the compound 30 (86.4 mg, 0.226 mmol) were added to a reaction flask, TBTU (80 mg, 0.25 mmol) was added under nitrogen protection, and dissolved by adding 2 mL of anhydrous DMF. DIPEA (87.6 mg, 0.34 mmol) was added dropwise in an ice bath. After the addition, the mixture was warmed to room temperature and stirred for 1 hour. After TLC detected the reaction was completed, the mixture was diluted with a small amount of water and extracted 3-4 times with EtOAc. The organic phases were combined, washed with brine, concentrated and then purified by silica gel column chromatography to give a product (88 mg, yield: 78.6%). LC-MS (APCI): m/z=498.4 (M+1)$^+$.

Step 5: Synthesis of (R)-(1-(2-(2,5-dichlorobenzamido)acetamido)-1-d-2,2-d2-3-methylbutyl)boronic Acid (compound I-5)

The compound 31 (88 mg, 0.177 mmol) and isobutylboronic acid (47 mg, 0.46 mmol) were added to a reaction flask, and dissolved by adding 1 mL of methanol and 1 mL of n-hexane. 1N hydrochloric acid (0.3 ml, 0.3 mmol) was added, and the reaction was stirred at room temperature under nitrogen protection overnight. After TLC detected the reaction was completed, the methanol layer was separated, washed three times with n-heptane, concentrated to dryness under reduced pressure, dissolved by adding a small amount of 2N sodium hydroxide, and washed three times with dichloromethane. The aqueous phase was adjusted to pH 2-3 with concentrated hydrochloric acid, and extracted 3-4 times with dichloromethane. The organic phases were combined, washed with brine, concentrated and then purified by silica gel column chromatography. The product was dried and weighed 32 mg (yield: 50.1%). LC-MS (APCI): m/z=346.4 (M+1-H$_2$O). $^1$H NMR (400 MHz, DMSO) δ 8.94 (t, J=5.9 Hz, 1H), 8.69 (s, 1H), 7.65 (s, 1H), 7.55 (d, J=1.4 Hz, 2H), 4.02 (d, J=5.8 Hz, 2H), 1.26 (m, 1H), 0.86-0.79 (m, 6H).

Example 6: Biological Activity Test

(1) 20S Proteasome Assay

25 μL of assay buffer containing human PA28 activator (Boston Biochem, final concentration 12 nM) and Ac-WLA-AMC ((35 selective substrate) (final concentration 15 μM) was added to 1 μL of test compounds dissolved in DMSO in a 384-well black microtiter plate at 37° C. Then, 25 μL of assay buffer containing human 20S proteasome (Boston Biochem, final concentration 0.25 nM) was added at 37° C. The assay buffer was consisted of 20 mM HEPES, 0.5 mM EDTA and 0.01% BSA with a pH of 7.4. The reaction was followed by a BMG Galaxy plate reader (37° C., 380 nm excitation, 460 nm emission, 20 gain). Percent inhibition was calculated based on the 0% inhibition (DMSO) and 100% inhibition (10 μM bortezomib) control groups.

The proteasome inhibitory action of the compounds disclosed herein was tested according to the above assay. It was observed that the compounds disclosed herein exhibited an inhibitory activity against the proteasome. The compounds disclosed herein have inhibitory activity against the proteasome with an IC$_{50}$ value of less than 50 nM.

(2) Metabolic Stability Evaluation

Experiments in microsomes: Human liver microsomes: 0.5 mg/mL, Xenotech; Rat liver microsomes: 0.5 mg/mL, Xenotech; Coenzyme (NADPH/NADH): 1 mM, Sigma Life Science; Magnesium chloride: 5 mM, 100 mM phosphate buffer (pH 7.4).

Preparation of stock solution: A certain amount of powder of the example compounds was accurately weighed and dissolved in DMSO to 5 mM respectively.

Preparation of phosphate buffer (100 mM, pH7.4): A pre-formulated 150 mL potassium dihydrogen phosphate (0.5 M) was mixed with 700 mL of dibasic potassium phosphate (0.5M). The pH of the mixture was adjusted to 7.4 with 0.5 M dibasic potassium phosphate solution. The mixture was diluted 5-fold with ultrapure water before use, and magnesium chloride was added to obtain the phosphate buffer (100 mM) containing 100 mM potassium phosphate, 3.3 mM magnesium chloride, pH 7.4.

A NADPH regeneration system solution (containing 6.5 mM NADP, 16.5 mM G-6-P, 3 U/mL G-6-P D, 3.3 mM magnesium chloride) was prepared and placed on wet ice before use.

Preparation of stop solution: acetonitrile solution containing 50 ng/mL propranolol hydrochloride and 200 ng/mL tolbutamide (internal standard). 25057.5 μL of phosphate buffer (pH 7.4) was taken into a 50 mL centrifuge tube, to which 812.5 μL human liver microsomes were added, respectively, and mixed to obtain a liver microsome dilution solution with a protein concentration of 0.625 mg/mL. 25057.5 μL of phosphate buffer (pH 7.4) was taken into a 50 mL centrifuge tube, to which 812.5 μL SD rat liver microsomes were added, respectively, and mixed to obtain a liver microsome dilution solution with a protein concentration of 0.625 mg/mL.

Incubation of the samples: The stock solution of the respective compounds was respectively diluted to 0.25 mM with an aqueous solution containing 70% acetonitrile, which were used as working solutions, ready for use. 398 μL of the dilution solution of human liver microsomes or rat liver microsomes were added to a 96-well incubation plate (N=2), respectively, and 2 μL of 0.25 mM working solution was added and mixed.

Metabolic stability assay: 300 μL of pre-chilled stop solution was added to each well of a 96-well deep well plate and placed on ice as the stop plate. The 96 well incubation plate and NADPH regeneration system were placed in a 37° C. water bath box, shaken at 100 rpm and pre-incubated for 5 min. 80 μL of incubation solution was taken out from each well of the incubation plate and added to the stop plate, mixed, and replenished with 20 μL of NADPH regeneration system solution as a 0-min sample. 80 μL of NADPH regeneration system solution was added to each well of the incubation plate to start the reaction and counting was started. The corresponding compounds had a reaction concentration of 1 μM and the protein concentration was 0.5 mg/mL. 100 μL of the reaction solution was taken at 10, 30, and 90 min after reaction, respectively, added to the stop plate, and vortexed for 3 minutes to terminate the reaction. The stop plate was centrifuged for 4 min at 5000× g at 4° C. 100 μL of the supernatant was added to a 96-well plate to which 100 μL of distilled water was previously added, mixed, and analyzed by LC-MS/MS.

Data analysis: The peak areas of the corresponding compounds and internal standard were detected by LC-MS/MS system, and the ratio of the peak area of the compounds to the internal standard was calculated. The slope was measured by plotting the natural logarithm of the percent of remained compound versus time, and $t_{1/2}$ and $CL_{int}$ were calculated according to the formula below, where V/M is equal to 1/protein concentration.

$$t_{1/2} = -\frac{0.693}{\text{Peak area}},$$

$$CL_{int} = \frac{0.693}{t_{1/2}} \cdot \frac{V}{M}.$$

The metabolic stability in human and rat liver microsomes was evaluated by simultaneously testing and comparing the compounds disclosed herein and the non-deuterated compound. The half-life and liver intrinsic clearance as indicators of metabolic stability are shown in the table. The non-deuterated compound Ixazomib was used as a control in the table. As shown in the table, the compounds disclosed herein can significantly improve the metabolic stability by comparison with Ixazomib in human and rat liver microsome experiments.

TABLE

Comparison Table of Indicators for Metabolic Stability of Compounds of Examples 1-4

| Number | Experiment in human liver microsomes | | Experiment in rat liver microsomes | |
|---|---|---|---|---|
| | $t_{1/2}$ | $CL_{int}$ | $t_{1/2}$ | $CL_{int}$ |
| Ixazomib | 28.1 | 49.4 | 14.3 | 97.3 |
| I-1 | — | — | 17.1 | 81.3 |
| I-2 | 29.8 | 46.5 | 15.3 | 90.5 |
| I-3 | 29.3 | 47.3 | — | — |
| I-4 | 28.7 | 48.3 | 15.4 | 90.0 |
| I-5 | 29.3 | 47.3 | 14.2 | 97.8 |

(3) Pharmacokinetic Experiment in Rats

Experimental objective: After administration of Ixazomib or Example compounds to rats, the pharmacokinetic behavior of the compounds disclosed herein was investigated.

Experimental Animals:
Species and strains: SD rat, grade: SPF grade
Gender and quantity: male, 6
Weight range: 180 to 220 g (the actual weight range was from 187 to 197 g)
Source: shanghai sippr bk laboratory animals ltd.
Laboratory and animal certificate number: SCXK (Shanghai) 2013-0016.

Experiment procedure:
Before blood samples were collected, 20 μL of 2 M sodium fluoride solution (esterase inhibitor) was previously added to an EDTA-K2 anticoagulant tube, dried in an 80° C. oven, and placed in a 4° C. refrigerator.

Rats (male, weighted 187 to 197 g) were randomly divided into 2 groups, and were fasted overnight in the afternoon before the experiment, but were allowed to drink water freely. Food was given 4 hours after the administration. Group A was given 3 mg/kg of Ixazomib, and group B was given 3 mg/kg of the Example compounds. About 100-200 μL of blood was taken from the orbital vein of rats at 15 min, 30 min, and 1, 2, 3, 5, 8 and 10 h after administration, placed in a 0.5 mL Eppendorf tube with EDTA-K2 anticoagulant and mixed immediately. After anticoagulation, the tube was gently inverted 5-6 times as quickly as possible. After the blood was taken, it was placed in an ice box, and then within 30 min, the blood sample was centrifuged for 10 min at 4000 rpm and at 4° C. to separate the plasma. Immediately after collection of all plasma, it was stored at −20° C. The concentration of the drug in plasma at each time point was determined after sample collection at all time points.

Based on the data obtained as described above (the average concentration of the drug in plasma after administration versus time), pharmacokinetics-related parameters of male SD rats after the i.g. administration of Ixazomib (3 mg/kg) and the Example compounds (3 mg/kg) were calculated using the Winnonin software according to non-compartment statistical moment theory.

The experiments showed that, as compared with Ixazomib, the compounds disclosed herein have excellent pharmacokinetic properties, and thus are more suitable as compounds for inhibiting proteasomes, and are further suitable for the preparation of a medicament for treating a proteasome-mediated disease.

It should be understood that these examples are only for illustrating the present disclosure and are not intended to limit the scope disclosed herein. Experimental methods that do not specify specific conditions in the examples are generally based on conventional conditions or conditions recommended by the manufacturer. Parts and percentages are parts by weight and percentages by weight unless otherwise indicated.

The above content is a further detailed description disclosed herein in combination with specific embodiments, and it cannot be assumed that the specific implementation disclosed herein is limited to these descriptions. For a person of ordinary skill in the art to which the present disclosure belongs, a number of simple deductions or substitutions can be made without departing from the concept disclosed herein, and should all be considered as falling within the protection scope disclosed herein.

What is claimed is:

1. A compound represented by Formula (I), or a crystalline form, a pharmaceutically acceptable salt, a prodrug, a stereoisomer, a hydrate or a solvate thereof,

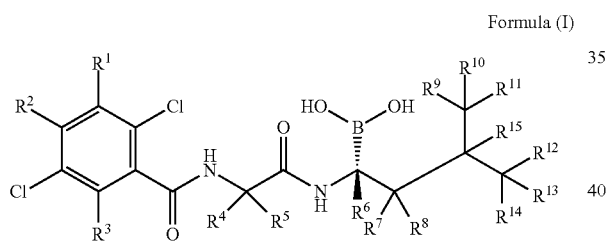

Formula (I)

wherein $R^4$, $R^5$, $R^6$, $R^7$, and $R^8$ are each independently hydrogen, deuterium, or halogen;
$R^1$, $R^2$, $R^3$, $R^9$, $R^{10}$, $R^{11}$, $R^{12}$, $R^{13}$, $R^{14}$, and $R^{15}$ are hydrogen;
provided that at least one of $R^4$, $R^5$, $R^6$, $R^7$, and $R^8$ is deuterium.

2. The compound according to claim 1, wherein $R^4$ and $R^5$ are deuterium.

3. The compound according to claim 1, wherein $R^6$ is deuterium.

4. The compound according to claim 2, wherein $R^6$ is deuterium.

5. The compound according to claim 1, wherein $R^7$ and $R^8$ are deuterium.

6. The compound according to claim 2, wherein $R^7$ and $R^8$ are deuterium.

7. The compound according to claim 3, wherein $R^7$ and $R^8$ are deuterium.

8. The compound according to claim 4, wherein $R^7$ and $R^8$ are deuterium.

9. The compound according to claim 1, wherein the compound is selected from the group consisting of the following compounds or a pharmaceutically acceptable salt thereof:

Formula (2)

Formula (3)

Formula (4)

Formula (5)

Formula (6)

Formula (7)

Formula (8)

10. The compound according to claim 1, wherein the compound is:

I-1 or a pharmaceutically acceptable salt thereof.

11. The compound according to claim 1, wherein the compound is:

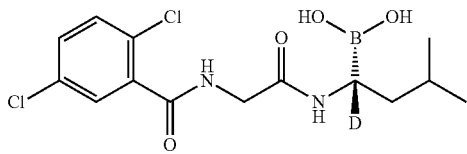

I-2 or a pharmaceutically acceptable salt thereof.

12. The compound according to claim 1, wherein the compound is:

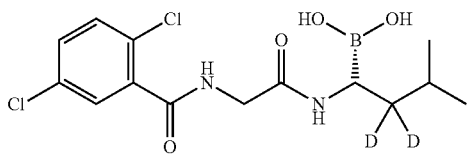

I-3 or a pharmaceutically acceptable salt thereof.

13. The compound according to claim 1, wherein the compound is:

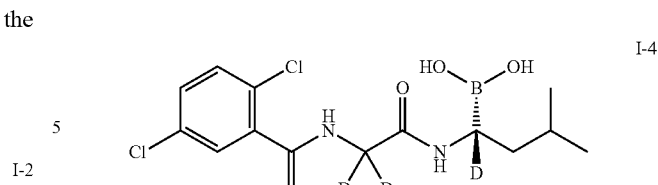

I-4 or a pharmaceutically acceptable salt thereof.

14. The compound according to claim 1, wherein the compound is:

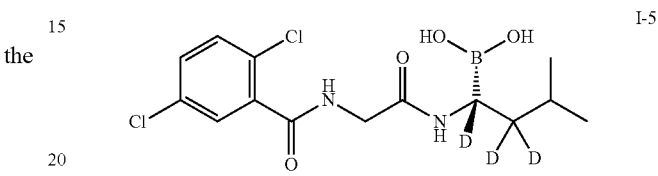

I-5 or a pharmaceutically acceptable salt thereof.

15. A pharmaceutical composition, comprising a pharmaceutically acceptable carrier, and a compound according to claim 1, or a crystalline form, a pharmaceutically acceptable salt, a hydrate, a solvate, a stereoisomer, or a prodrug.

16. A pharmaceutical composition, comprising a pharmaceutically acceptable carrier, and a compound according to claim 9, or a pharmaceutically acceptable salt thereof.

* * * * *